United States Patent
Daniel et al.

(12) 
(10) Patent No.: US 6,315,774 B1
(45) Date of Patent: Nov. 13, 2001

(54) MINIMALLY INVASIVE APPARATUS FOR FORMING REVASCULARIZATION CHANNELS

(75) Inventors: Steve A. Daniel, Fremont; Richard L. Mueller, Byron, both of CA (US); Robert D. Dowling, Louisville, KY (US)

(73) Assignee: Eclipse Surgical Technologies, Inc., Sunnyvale, CA (US)

( * ) Notice: Subject to any disclaimer, the term of this patent is extended or adjusted under 35 U.S.C. 154(b) by 0 days.

(21) Appl. No.: 09/457,461

(22) Filed: Dec. 8, 1999

Related U.S. Application Data

(60) Division of application No. 08/794,733, filed on Feb. 3, 1997, now Pat. No. 6,027,497, and a continuation-in-part of application No. 08/627,704, filed on Mar. 29, 1996, now Pat. No. 5,725,523.

(51) Int. Cl.⁷ .................................................... A61B 18/18
(52) U.S. Cl. .................................. 606/15; 606/7; 606/28; 600/104; 600/146
(58) Field of Search ...................................... 600/104, 146; 606/13–15, 7, 8, 2, 28, 41, 167–170; 607/88–89, 92, 93, 96, 98, 100, 113

(56) References Cited

U.S. PATENT DOCUMENTS

| 4,072,147 | 2/1978 | Hett .......................................... 128/6 |
| 4,418,688 | 12/1983 | Loeb . | |

(List continued on next page.)

FOREIGN PATENT DOCUMENTS

| 29610320 | 6/1996 | (DE) . |
| WO 93/20742 | 10/1993 | (WO) . |
| wo 97/25101 | 7/1997 | (WO) . |

OTHER PUBLICATIONS

Rissel, U. et al., "A New 2–Channel Stimulation Device with Integrated Ablation–control Unit for the Diagnosis and Treatment of Cardiac Arrythmias," Biomed. Technik 33 (1988) pp. 18–25.

English Translation of Biomed. Technik Article.

Abela et al., Effects of Carbon Dioxide, Nd–YAG, and Argon Laser Radiation on Coronary Atheromatous Plaques, The American Journal of Cardiology, vol. 50, Dec. 1982, pp. 1199–1205.

Abela et al. Laser Recanalization of Occluded Atherosclerotic Arteries In Vivo and In Vitro, Laboratory Investigation, Coronary Artery Disease, vol. 71, No. 2, Feb. 1985, pp.. 403–411.

(List continued on next page.)

*Primary Examiner*—Roy Gibson
(74) *Attorney, Agent, or Firm*—Gibson, Dunn & Crutcher LLP

(57) ABSTRACT

An apparatus for performing transmyocardial revascularization provides a closed-chest formation of a channel in a wall of a heart. An articulating scope in one embodiment includes a flexible distal portion which provides for a coupling of a surface of the heart to the distal portion. The articulating distal portion is coupled to a control member to provide articulation. Movement of the control member causes deflection, including articulation, of the generally flexible working end of the scope. The coupler may be a two way valve to provide both vacuum and flushing solutions. The articulating scope can be supported by a scope holder that is table mounted or mounted to the patient. An access port provides for the introduction of tools and instruments. An adaptor couples the access port with a handle. The handle provides a working channel for the introduction of an energy delivery device.

17 Claims, 8 Drawing Sheets

U.S. PATENT DOCUMENTS

| | | |
|---|---|---|
| 4,448,188 | 5/1984 | Loeb . |
| 4,453,547 * | 6/1984 | Cartel et al. .................... 128/421 |
| 4,538,613 | 9/1985 | Rosenberg . |
| 4,641,650 | 2/1987 | Mok . |
| 4,641,912 | 2/1987 | Goldenberg . |
| 4,648,892 | 3/1987 | Kittrell et al. . |
| 4,654,024 | 3/1987 | Crittenden et al. . |
| 4,658,817 | 4/1987 | Hardy .................... 128/303.1 |
| 4,669,467 | 6/1987 | Willett et al. . |
| 4,676,231 | 6/1987 | Hisazumi et al. . |
| 4,682,594 | 7/1987 | Mok . |
| 4,693,556 | 9/1987 | McCaughan, Jr. . |
| 4,706,656 | 11/1987 | Kuboto . |
| 4,718,417 | 1/1988 | Kittrell et al. . |
| 4,719,912 | 1/1988 | Weinberg . |
| 4,745,920 | 5/1988 | Forssman et al. . |
| 4,785,815 | 11/1988 | Cohen . |
| 4,788,975 * | 12/1988 | Shturman et al. .................... 606/7 |
| 4,827,906 | 5/1989 | Robicsek et al. . |
| 4,850,351 | 7/1989 | Herman et al. . |
| 4,860,743 | 8/1989 | Abela . |
| 4,890,898 | 1/1990 | Bentley et al. . |
| 4,899,732 * | 2/1990 | Cohen . |
| 4,913,142 | 4/1990 | Kittrell et al. . |
| 4,917,084 | 4/1990 | Sinofsky . |
| 4,966,148 | 10/1990 | Millar . |
| 4,967,745 | 11/1990 | Hayes et al. . |
| 4,976,710 * | 12/1990 | Mackin .................... 606/15 |
| 4,985,029 | 1/1991 | Hoshino . |
| 4,997,431 | 3/1991 | Isner et al. . |
| 5,041,108 * | 8/1991 | Fox et al. .................... 606/15 |
| 5,093,877 | 3/1992 | Aita et al. . |
| 5,106,386 | 4/1992 | Isner et al. . |
| 5,125,926 * | 6/1992 | Rudko et al. .................... 606/19 |
| 5,217,454 * | 6/1993 | Khoury .................... 606/14 |
| 5,249,574 * | 10/1993 | Bush et al. .................... 607/9 |
| 5,336,215 * | 8/1994 | Hsueh et al. .................... 606/4 |
| 5,380,316 | 1/1995 | Aita et al. .................... 606/7 |
| 5,389,096 | 2/1995 | Aita et al. .................... 606/15 |
| 5,397,321 * | 3/1995 | Houser et al. .................... 606/41 |
| 5,401,272 * | 3/1995 | Perkins .................... 605/15 |
| 5,425,355 * | 6/1995 | Kulick .................... 606/14 |
| 5,431,628 | 7/1995 | Millar . |
| 5,454,807 * | 10/1995 | Lennox et al. .................... 606/15 |
| 5,503,156 | 4/1996 | Millar . |
| 5,549,601 * | 8/1996 | McIntyre et al. .................... 606/15 |
| 5,554,152 | 9/1996 | Aita et al. . |
| 5,573,531 * | 11/1996 | Gregory .................... 606/14 |
| 5,582,190 * | 12/1996 | Slavin et al. .................... 606/15 |
| 5,607,421 * | 3/1997 | Jeevanandam et al. .................... 606/15 |
| 5,667,476 * | 9/1997 | Frassica et al. .................... 600/149 |
| 5,672,170 | 9/1997 | Cho et al. . |
| 5,713,894 * | 2/1998 | Murphy-Chutorian et al. ........ 606/10 |
| 5,725,523 | 3/1998 | Mueller .................... 606/15 |
| 6,001,091 | 12/1999 | Murphy-Chutorian et al. ......... 606/1 |
| 6,027,497 | 2/2000 | Daniel et al. .................... 606/15 |

OTHER PUBLICATIONS

Anderson et al., Coaxial Laser Energy Delivery Using a Steerable Catheter in Canine Coronary Arteries, American Heart Journal, Jan 1987, pp. 37–48.

H.T. Aretz et al., Intraluminal Ultrasound Guidance of Transverse Laser Coronary Atherectomy, SPIE vol. 1201 Optical Fibers in Medicine V (1990), pp. 68–78.

Bogen et al., Is Catheter Ablation on Target, The American Journal of Cardiology, vol. 60, Dec. 1, 1987, pp. 1387–1392.

Bommer et al., Laser Atrial Septostomy, American Heart Journal, Nov. 1983, pp. 1152–1156.

Bowker et al., Laser Assisted Coronary Angioplasty, European Heart Journal, ©1988, pp. 25–29.

Choy et al., Laser Coronary Angioplasty: Experience with 9 Cadaver Hearts, The American Journal of Cardiology, vol. 50, Dec. 1982, pp. 1209–1211.

Choy et al., Transluminal Laser Catheter Angioplasty, The American Journal of Cardiology, vol. 50, Dec. 1982, pp. 1206–1208.

Cox et al., Laser Photoablation for the Treatment of Refractory Ventricular Tachycardia and Endocardial Fibroelastosis, The Annals of Thoracic Surgery, vol. 39, No. Mar. 1985, pp. 199–200.

Davi et al., Continuous Wave (CW) and Pulsed Laser Effects on Vascular Tissues and Occlusive Disease in Vitro, Lasers in Surgery and Medicine 5:239–250 ©1985 Alan R. Liss, Inc.

Desilets et al., A New Method of Percutaneous Catheterization, Radiology, 85 Jul. 1965, pp. 147–148.

Goda et al., Myocardial Revascularization by CO2 Laser, ©1987 S. Karger AG Basel, Eur. surg. REs. 19;pp. 113–117

Grundfest et al., Laser Ablation of Human Atherosclerotic Plaque Without Adjacent Tissue Injury, Laser Angioplasty: Morphologic Studies, *JACC*, Apr. 1985, pp. 929–933.

Hardy et al., Regional Myocardial Blood Flow and Cardiac Mechanics in Dog Hearts with $CO_2$Laser–induced Intramyocardial Revascularization, Basic Research in Cardiology, vol. 85, No. 2, 1990, pp. 179–197.

Isner et al., Identification of Photoproducts Liberated by In Vitro Argon Laser Irradiation of Atherosclerotic Plaque, Calcified Cardiac Valves and Myocardium, The American Journal of Cardiology, Apr. 1985, pp.1192–1196.

Isner et al., Laser–Assisted Debridement of Aortic Valve Calcium, American Heart Journal, Mar. 1985, pp. 448–452.

Isner et al., Laser–Assisted Endocardiectomy for Refractory Ventricular Tachyarrhythmias: Preliminary Intraoperative Experience, Clinical Cardiology vol. 10, Mar. 1987, pp. 201–204.

Isner, et al., Laser Myoplasty for Hypertrophic Cardiomyopathy, Jun. 1, 1984, The American Journal of Cardiology, vol. 53, pp. 1620–1625.

Isner et al., Laser Photoablation of Pathological Endocardium: In Vitro Findings Suggesting a New Approach to the Surgical Treatment of Refractory Arrhythmias and Restrictive Cardiomyopathy, The Annals of Thoracic Surgery, vol. 39, No. 3, Mar. 1985, pp. 201–206.

Jeevanandam et al., Myocardial Revascularization by Laser––Induced Channels, Surgical Forum XLI, Oct. 1990, pp. 225–227.

Josephson et al., Endocardial Excision: A New Surgical Technique for the Treatment of Recurrent Ventricular Tachycardia, Circulation, vol. 60, No. 7, Dec. 1979, pp. 1430–1439.

Kjellstrom et al., The Use of Lasers in Vascular and Cardiac Surgery, Acta Chir Scand 153, 1987, pp. 493–499.

Lee et al., Effects of Laser Irradiation Delivered by Flexible Fiberoptic System on the Left Ventricular Internal Myocardium, Sep., 1983, American Heart Journal, pp. 587–590.

Lee et al., Laser–Dissolution of Coronary Atherosclerotic Obstruction, American Heart Journal, Dec. 1981, pp. 1074–1075.

Lee et al., Potential Complications of Coronary Laser Angioplasty, American Heart Journal, Dec. 1984, pp. 1577–1579.

Lee et al., Transcatheter Ablation: Comparison between Laser Photoblation and Electrode Shock Ablation in the Dog, Mar. 1985, Laboratory Investigation, Laser Photoablation, vol. 71, pp. 579–586.

Masayoshi et al., Current Problems in Coronary Artery Surgery: New Methods for Myocardial Revascularization and Vascular Anastomosis, Jan., 1960, pp. 1203–1207.

Mirhoseini et al., Clinical and Histological Evaluation of Laser Myocardial Revascularization, Journal of Clinical Laser Medicine & Surgery, Jun. 1990, pp. 73–78.

Mirhoseini et al., Clinical Report: Laser Myocardial Revascularization, © Alan R. Liss, Inc., Lasers in Surgery and Medicine 6:459–461 (1986).

Mirhoseini, Laser Applications in Thoracic and Cardiovascular Surgery, Medical Instrumentation, vol. 17, No. 6, 11–12, 1983, © 1983 Association for the Advancement of Medical Instrumentation.

Mirhoseini, Laser Revascularization of the Heart, New Frontiers in Laser Medicine and Surgery, ISBN Elsevier Science Publishing Co., pp. 296–303.

Mirhoseini et al., Lasers in Cardiothoracic Surgery, Chapter 21, pp. 216–232.

Mirhoseini et al., Myocardial Revascularization by Laser: A Clinical Report, © 1983 Alan R. Liss, Inc., Lasers in Surgery and Medicine 3:241–245.

Mirhoseini et al., New Concepts in Revascularization of the Myocardium, The Annals of Thoracic Surgery, vol. 45, No. 4, Apr. 1988, pp. 415–420.

Mirhoseini et al., Revascularization of the Heart by Laser, Journal of Microsurgery, Jun. 1981, pp. 253–260.

Mirhoseini, Transventricular Revascularization by Laser, Lasers in Surgery and Medicine, 2:187–198(1982).

Okada et al., Alternative Method of Myocardial Revascularization by Laser: Experimental and Clinical Study, Kobe J. Medical Science 32, Oct. 1986, pp. 151–161.

Regna, Abstract of U.S. Patent Application No. 4, 796,630; Filed: Jan. 10, 1989.

Riemenschneider et al., Laser Irradiation of Congenital Heart Disease: potential for Palliation and Correction of Intracardiac and Intravascular Defects, American Heart Journal, Dec. 1983, pp. 1389–1393.

Saksena et al., Laser Ablation of Normal and Diseased Human Ventricle, Jul. 1986, American Heart Journal, pp. 52–60.

Selle et al., Successful Clinical Laser Ablation of Ventricular Tachycardia: A Promising New Therapeutic Methoc, Ann Thorac Surg, Oct. 1986, pp. 380–384.

Svenson et al., Neodymium: YAG Laser Photocoagulation: A Successful New Map–Guided Technique for the Intraoperative Ablation of Ventricular Tachycardia, Therapy and Prevention–Laser Photocoagulation, vol. 76, No. 6, Dec. 1987, pp. 1319–1328.

van Gemert et al., Optical Properties of Human Blood Vessel Wall and Plaque, Lasers in Surgery and Medicine, vol. 5, 1985, pp. 235–237.

White, Angioscopy and Lasers in Cardiovascular Surgery: Current Applications and Future Prospects, Aust. N.Z., Surg. 1988, pp. 271–274.

Zeevi et al., The Use of Carbon Dioxide Fiberoptic Laser Catheter for Atrial Septostomy, American Heart Journal, Jul. 1988, pp. 117–122.

* cited by examiner

MINIMALLY INVASIVE APPARATUS FOR FORMING REVASCULARIZATION CHANNELS

CROSS-REFERENCE TO RELATED APPLICATIONS

This application is a divisional of U.S. patent application Ser. No. 08/794,733 entitled Minimally Invasive Method for Forming Revascularization Channels filed Feb. 3, 1997 now U.S. Pat. No. 6,027,497continuation-in-part of U.S. Ser. No. 08/627,704 now U.S. Pat. No. 5,725,523, entitled "LATERAL-AND POSTERIOR-ASPECT METHOD AND APPARATUS FOR LASER-ASSISTED TRANSMYOCARDIAL REVASCULARIZATION AND OTHER SURGICAL APPLICATIONS", filed Mar. 29, 1996, incorporated herein by reference, and is related to application Ser. No. 08/793,000, entitled "REVASCULARIZATION WITH HEART PACING", now U.S. Pat. No. 6,001,091, which is incorporated herein by reference.

BACKGROUND OF THE INVENTION

1. Field of the Invention

This invention relates to transmyocardial REVASCULARIZATION ("TMR"), and more particularly to a TMR method that introduces an energy delivery device through a minimally invasively formed penetration of a patient's chest.

2. Description of Related Art

The human heart is a muscular dual pump that beats continuously throughout life sending blood to the lungs and the rest of the body. The interior of the heart consists of four distinct chambers. The septum, a thick central muscular wall, divides the cavity into right and left halves. On the right side, the upper half is known as the right atrium. Deoxygenated blood from the rest of the body arrives in the right atrium via the vena cava, the blood is pumped across a one-way valve known as the tricuspid valve into the lower portion known as the right ventricle. From there the blood circulates to the lungs through the pulmonary valve via the pulmonary artery where it is oxygenated by circulation through the alveoli of the lungs (not shown). The blood returns via the pulmonary veins to the left atrium and flows through a second valve, the mitral valve into the left ventricle where it is pumped via the aorta to the rest of the body.

Much of the heart consists of a special type of muscle called myocardium. The myocardium requires a constant supply of oxygen and nutrients to allow it to contract and pump blood throughout the vasculature. The inner surfaces of the chambers of the heart are lined with a smooth membrane, the endocardium, and the entire heart is enclosed in a tough, membranous bag known as the pericardial sac.

The pumping action of the heart has three main phases for each heart beat. Diastole is the resting phase during which the heart fills with blood: while deoxygenated blood is entering the right atrium, oxygenated blood is returned from the lungs to the left atrium. During atrial systole, the two atria contract simultaneously, squeezing the blood into the lower ventricles. Finally, during ventricular systole the ventricles contract to pump the deoxygenated blood into the pulmonary arteries and the oxygenated blood into the main aorta. When the heart is empty, diastole begins again. The electrical impulses which stimulate the heart to contract in this manner emanate from the heart's own pacemaker, the sinoatrial node. The heart rate is under the external control of the body's autonomic nervous system.

Though the heart supplies blood to all other parts of the body, the heart itself has relatively little communication with the oxygenated blood supply. Thus, the two coronary arteries, the left coronary artery and the right coronary artery, arise from the aorta and encircle the heart muscle on either side "like a crown" to supply the heart itself with blood.

Heart disorders are a common cause of death in developed countries. They also impair the quality of life of millions of people and restrict activity by causing pain, breathlessness, fatigue, fainting spells and anxiety. The major cause of heart disease in developed countries is impaired blood supply. The coronary arteries become narrowed due to atherosclerosis and part of the heart muscle is deprive of oxygen and other nutrients. The resulting ischemia or blockage can lead to *angina pectoris*, a pain in the chest, arms or jaw due to a lack of oxygen to the heart, or infarction, death of an area of the myocardium caused by the ischemia.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be relieved in a number of ways. Drug therapy, including nitrates, beta-blockers, and peripheral vasodilator drugs (to dilate the arteries) or thrombolytic drugs (to dissolve clots) can be very effective. If drug treatment fails transluminal angioplasty is often indicated—the narrowed part of the artery, clogged with atherosclerotic plaque or other deposits, can be stretched apart by passing a balloon to the site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion, thereby requiring emergency procedures), the procedure known as coronary artery bypass grafting (CABG) may be indicated. CABG is the most common and successful major heart operation performed, with over 500,000 procedures being performed annually in America alone. The procedure takes at least two surgeons and can last up to five hours. First, the surgeon makes an incision down the center of the patient's chest and the heart is exposed by opening the pericardium. A length of vein is removed from another part of the body, typically the leg. The patient is connected to a heart-lung machine which takes over the function of the heart and lungs during the operation. The section of vein is first sewn to the aorta and then sewn onto a coronary artery at a place such that oxygenated blood can flow directly into the heart. The patient is then closed. Not only does the procedure require the installation of the heart-lung machine, a very risky procedure, but the sternum must be sawed through and the risk of infection is enhanced during the time the chest cavity is spread open.

Another method of improving myocardial blood supply is called transmyocardial REVASCULARIZATION (hereafter "TMR"), the creation of channels from the epicardial to the endocardial portions of the heart. The procedure uses needles in a form of "myocardial acupuncture," has been experimented with at least as early as the 1930s and used clinically since the 1960s. Deckelbaum. L. I., Cardiovascular Applications of Laser technology, *Lasers in Surgery and*

Medicine 15:315–341 (1994). The technique was said to relieve ischemia by allowing blood to pass from the ventricle through the channels either directly into other vessels perforated by the channels or into myocardial sinusoids which connect to the myocardial microcirculation. The procedure has been likened to transforming the human heart into one resembling that of a reptile.

In the reptile heart, perfusion occurs via communicating channels between the left ventricle and the coronary arteries. Frazier, O. H., Myocardial REVASCULARIZATION with Laser—Preliminary Findings, Circulation, 1995, 92 [suppl II:II-58-II-65]. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous studies have been performed on TMR using lasers to bore holes in the myocardium. The exact mechanism by which blood flows into the myocardium is not well understood however. In one study, 20–30 channels per square centimeter were bored into the left ventricular myocardium of dogs prior to occlusion of the arteries. LAD ligation was conducted on both the revascularized animals as well as a set of control animals. Results showed that animals having undergone TMR prior to LAD ligation acutely showed no evidence of ischemia or infarction in contrast to the control animals. After sacrifice of the animals post operatively between 4 weeks and 5 months, the laser-created channels could be demonstrated grossly and microscopically to be open and free of debris and scarring.

It is believed that the TMR channels occlude toward the epicardial surface but that their subendocardial section remains patent (unobstructed) and establishes camerosinusoidal connections. It is possible that the creation of laser channels in the myocardium may promote long-term changes that could augment myocardial blood flow such as by inducing angiogenesis in the region of the lazed (and thus damaged) myocardium. Support for this possibility is reported in histological evidence of probable new vessel formation adjacent to collagen occluded transmyocardial channels. In the case of myocardial acupuncture or boring, which mechanically displaces or removes tissue, acute thrombosis followed by organization and fibrosis of clots is the principal mechanism of channel closure. By contrast, histological evidence of patent, endothelium-lined tracts within the laser-created channels supports the assumption that the inside of the laser channels is or can become hemocompatible and that it resists occlusion caused by thrombo-activation and/or fibrosis. A thin zone of charring occurs on the periphery of the laser-created transmyocardial channels through the well-known thermal effects of optical radiation on cardiovascular tissue. This type of interface may inhibit the immediate activation of the intrinsic clotting mechanisms because of the inherent hemocompatibility of carbon. In addition, the precise cutting action that results from the high absorption and low scattering of laser energy ($CO_2$, HO, etc.) may minimize structural damage to collateral tissue, thus limiting the tissue thromboplastin-mediated activation of the extrinsic coagulation.

U.S. Pat. No. 4,658,817 issued Apr. 21, 1987 to Hardy teaches a method and apparatus for TMR using a laser. A surgical $CO_2$ laser includes a handpiece for directing a laser beam to a desired location. Mounted on the forward end of the handpiece is a hollow needle to be used in surgical applications where the needle perforated a portion of tissue to provide the laser beam direct access to distal tissue.

U.S. Pat. No. 5,125,926 issued Jun. 30, 1992 to Rudko et al. teaches a heart-synchronized pulsed laser system for surgical TMR. The device and method comprises a device for sensing the contraction and expansion of a beating heart. As the heart beat is monitored, the device triggers a pulse of laser energy to be delivered to the heart during a predetermined portion of the heartbeat cycle. This heart-synchronized pulsed laser system is important where the type of laser, the energy and pulse rate are potentially damaging to the beating heart or its action. Often, application of laser energy to a beating heart can induce fibrillation or arrhythmia. Additionally, as the heart beats, its spatial relationship between the heart and the tip of the laser delivery probe may change so that the necessary power of the beam and the required position of the handpiece may be unpredictable.

Finally, U.S. Pat. Nos. 5,380,316 issued Jan. 10, 1995 and U.S. Pat. No. 5,389,096 issued Feb. 14, 1995 both to Aita et al. teach systems and methods for intra-operative and percutaneous myocardial REVASCULARIZATION, respectively. The former patent is related to TMR performed by inserting a portion of an elongated flexible lasing apparatus into the chest cavity of a patient and lasing channels directly through the outer surface of the epicardium into the myocardium tissue. In the latter, TMR is performed by guiding an elongated flexible lasing apparatus into a patient's vasculature such that the firing end of the apparatus is adjacent the endocardium and lases channels directly through the endocardium into the myocardium tissue without perforating the pericardium layer. None of the above patents teach any method for performing TMR in a minimally invasive surgical procedure, nor do they teach methods of visualizing the areas of the heart being lazed, nor do they teach any method or devices for achieving TMR on surfaces or portions of the heart which are not directly accessible via a sternotomy, mini-sternotomy or via a trocar.

There is a need for a method and apparatus for performing TMR with one or more minimally invasively formed penetrations and eliminating the need for opening the chest cavity.

SUMMARY OF THE INVENTION

Accordingly, an object of the invention is to provide a method and apparatus for performing TMR.

Another object of the invention is to provide a method and apparatus for minimally invasively performing TMR.

Yet another object of the invention is to provide a method and apparatus for performing TMR through a minimally invasively formed penetration of a patient's chest.

Still another object of the present invention is to provide a method and apparatus for performing TMR through a single minimally invasively formed penetration of a patient's chest.

A further object of the present invention is to provide a method and apparatus for performing TMR through two minimally invasively formed penetrations of a patient's chest.

Still a further object of the present invention is to provide a method and apparatus for performing TMR through three minimally invasively formed penetrations of a patient's chest.

Another object of the present invention is to provide a method and apparatus for performing TMR through a minimally invasively formed penetration in a patient's chest with an articulating scope that includes at least one working channel.

Yet another object of the present invention is to provide a method and apparatus for TMR through first and second minimally invasively formed penetrations in a patient's chest with an articulating scope in the first penetration and a trocar configured to introduce working tools through the second penetration.

A further object of the invention is provide a method and apparatus for TMR by forming one or more minimally invasively formed penetrations and provide access to more than one region of the heart.

These and other objects of the invention are achieved in a method for a closed-chest formation of a channel in a wall of a heart. An energy delivery device is introduced through a first minimally invasive penetration of a patient's chest. Sufficient energy is delivered from the energy delivery device to the wall of the heart to form a channel through at least a portion of the wall. In its simplest embodiment, a conventional pneumo needle may be inserted through the chest wall and a laser waveguide inserted therethrough to form a channel, preferably using a viewing apparatus to show the position of the advancing waveguide and the heart wall.

In one embodiment of the invention a method of closed-chest formation of a channel in a wall of a heart includes introducing a first visualization apparatus through a first minimally invasive penetration of a patient's chest. The first visualization apparatus includes a working channel. An energy delivery device is introduced through the working channel of the first visualization device. Sufficient energy is delivered from the energy delivery device to the wall of the heart to form a channel through at least a portion of the wall.

In another embodiment of the invention, A method of closed-chest formation of a channel in a wall of a heart includes forming first, second and third minimally invasive penetrations in a patient's chest. A first visualization device is introduced through the first minimally invasive penetration. The heart is prepared for channel formation by using tools introduced through the second and third minimally invasive penetrations. A second visualization device includes a working channel and is introduced through the third minimally invasive penetration. An energy delivery device is introduced through either the second minimally invasive penetration or the working channel of the second visualization device. Sufficient energy from the energy delivery device is delivered to the wall of the heart and form a channel through at least a portion of the wall.

In another embodiment, a TMR energy delivery system includes a reusable visualization member. A TMR energy delivery device is removably mounted to the reusable visualization member. The TMR energy delivery device includes a distal section and is configured to deliver a sufficient level of energy to create a channel in a heart wall.

The positioning of the visualization devices and the working tools can be interchanged between the first, second and third minimally invasively formed penetrations.

DETAILED DESCRIPTION

The present invention provides a method and apparatus for a closed-chest formation of a REVASCULARIZATION channel in a wall of a heart. An energy delivery device is introduced through a first minimally invasive penetration of a patient's chest. Sufficient energy is delivered from the energy delivery device to the wall of the heart to form a channel through at least a portion of the wall. One, two, three, or more minimally invasively formed penetrations are formed in the patient's chest. One or more visualization devices are used. Working tools are introduced through one of the penetrations to prepare the heart for the creation of revascularizations channels. The first visualization device can be a rigid scope which provides a desired viewing of most or all the exterior of the heart to identify larger coronary vessels, presence of pericardium, adhesions and the like. The second visualization device is preferably an articulating scope with a working channel which allows identification of smaller coronary vessels to be avoided during TMR. The functions of both scopes can be combined in the articulating scope. REVASCULARIZATION channel formation can proceed with the energy delivery device being introduced through any of the first, second or third minimally invasively formed penetrations that are made.

For purposes of the present invention, a minimally invasively formed penetration means a penetration that is not large, does not involve opening the chest, spreading ribs and cutting through ribs and/or the sternum. Minimally invasive also includes the formation of penetrations that may be performed intercostally or non-intercostally and going inside out to create channels in the ventricle from the inside tissue of the endocardium. "Channels" refers to revascularization entries through the epicardium or myocardium and further includes entries that extend (i) all the way through the endocardium from the epicardium; (ii) partially through the myocardium from the epicardium; (iii) stimulation zones; (iv) drug pockets; or (v) from the endocardium, fully or partially through the myocardium.

Figure 1:
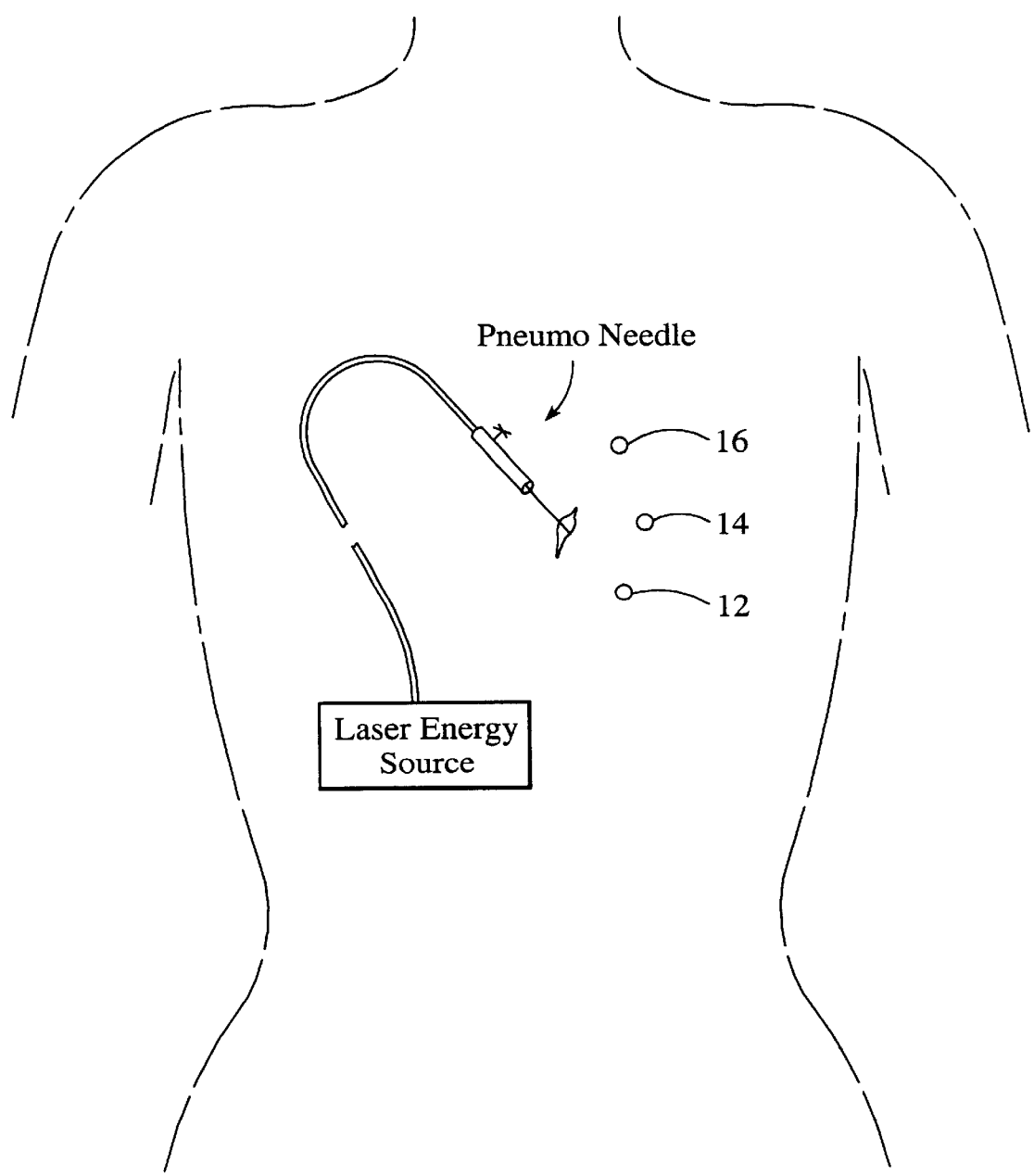
FIG. 1 is a perspective view of a patient illustrating first, second and third minimally invasive formed penetrations formed in the patient's chest and used to create REVASCULARIZATION channels, as well as the introduction of a pneumo needle.

Referring now to FIG. 1, a perspective view of a patient 10 is shown with first, second and third minimally invasively formed penetrations 12, 14 and 16 respectively. It will be appreciated that the exact location of penetrations 12, 14 and 16 is not limited to those illustrated in FIG. 1. Additionally, from 1 to N+1 numbers of penetrations may be made.

The patient is prepared for the procedure and is positioned similarly to that used for a left thoracotomy. The patient's left arm is draped. A conventional double lumen endotracheal tube is used to selectively deflate one side or the other of the lungs. Preferably the left lung is collapsed which allows access to the chest cavity in the vicinity of the left lung. The other lung remains inflated to provide oxygenation.

In various embodiments of the present invention, a distal portion of the energy delivery device is positioned to reach a desired aspect of a ventricular wall. A plurality of different REVASCULARIZATION channels are formed in the heart. A distal portion of the energy delivery device can be positioned against tissue of the wall of the heart through which the channel is to be formed while transmitting energy from a remote energy source through the energy delivery device. Suitable energy delivery devices include but are not limited to laser wave guides, RF electrodes, microwave cutters, ultrasound transmitters, mechanical coring devices, fluid jets and the like. Each energy delivery device is configured to be coupled to an energy source including but not limited to RF, laser, microwave, ultrasound, mechanical coring, fluid jet, cryogenic fluid, chemical ablation and the like. The distal portion of the energy delivery device can be urged against the heart wall while energy is delivered through the energy delivery device. Additionally, instead of the energy delivery device making physical contact with the heart wall the energy delivery device can deliver energy through a gaseous medium to the heart wall Additionally, the waveguide may be configured to pierce the epicardium so that energy is delivered to the myocardium. A REVASCULARIZATION channel can be formed through an epicardium into at least a portion of a myocardium or continue through the myocardium into all or only a portion of the endocardium.

In one embodiment, penetration 12 is used for the introduction of a rigid scope which can be, for example, a standard 10 mm laparoscope or thorascope. A suitable rigid scope is available from STRYRER, WOLF, or STORZ. The rigid scope provides a global view of an internal chest area of interest. For standard TMR at the apex region of the heart, a first penetration 12 can be from the fourth to sixth intercostal space and may be 10 to 12 mm in diameter. A slight cut-down is made and a standard thoracic trocar is advanced through the chest. A rigid scope typically found in an operating room is then inserted. Commonly available rigid scopes can be zero to 60 degree scopes such as the STORZ 26003AA 0° 10 mm×3/cm scope, or STORZ 26003BA 30°, 10 mm×3/cm. Other rigid or articulating scopes are also suitable.

A 30 degree rigid scope may be used for a narrow chest cavity because there a limited amount of chest cavity space is available. Additionally, the 30 degree scope permits bending. Choice of rigid scope is a surgical preference by the practitioner.

The rigid scope is used to visualize the area, look for larger coronary vessels, to inspect the condition of the pericardium, and to check for adhesions. The shape of the heart as well as its position is visualized. Second penetration 14 is formed inferior to penetration 12 and can be formed just above the diaphragm and third penetration 16 is formed superior to penetration 12. Penetrations 14 and 16 can be formed substantially the same way as penetration 12 is formed or may be cut downs only.

Figure 2:
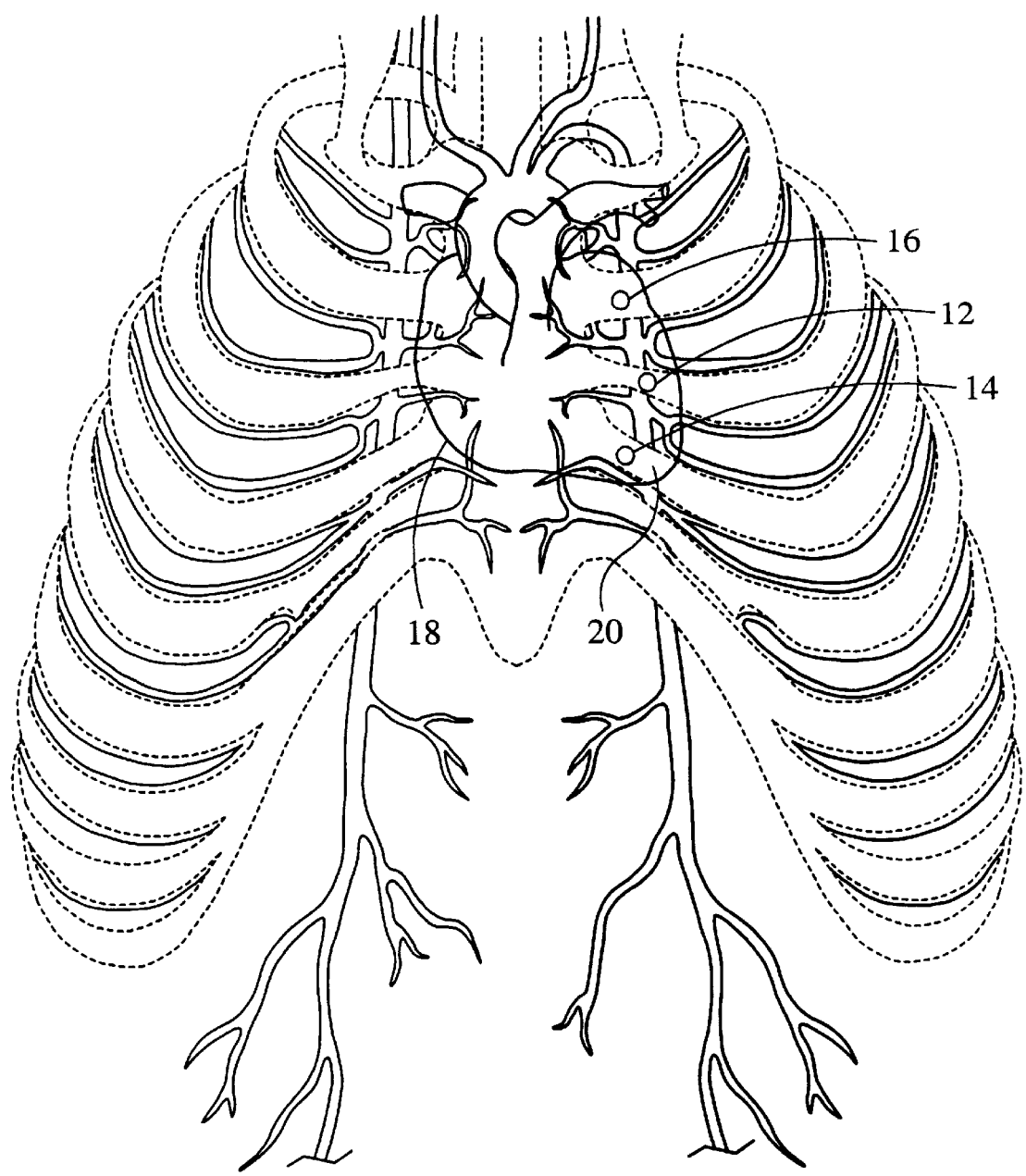
FIG. 2 is a perspective view of an interior of the patient's chest illustrated in FIG. 1.

For initial procedures a pair of thoracoscopic graspers may be introduced through penetration 14. Additional tools that can be introduced through penetration 14 include scissors. The pericardial sac 18 (FIG. 2), if intact, is grabbed and opened up by making a stem to stern type of incision. The pericardial sac is pulled away from the heart and may be suspended. Any unwanted adhesions are removed.

After the tools are removed from penetration 14, an articulating scope, with working channel, is introduced. A suitable articulating scope is a bronchoscope. The articulating scope may be a digital scope where the CCD portion is at the far end so it does not require additional optics throughout the length of the scope. This provides a camera at the articulating scope's tip. When the functionality of the rigid scope is incorporated into the articulating scope then the need for the rigid scope is then eliminated. Additionally, the articulating scope can be inserted in the first penetration and the rigid scope can be inserted into second penetration 14 after the tools are removed from second penetration 14. The articulating scope generally provides a view sufficient to visualize and avoid small coronary arteries.

Third penetration 16 is formed, a trocar introduced and a pair of forceps places an absorbing medium, including but not limited to a piece of gauze through the third penetration 16. Third penetration 16 is created initially to open the pericardial sac and subsequently may be used as a treatment port, for visualization or for safety reasons. In the event that a structure, such as a coronary artery is nicked and bleeding is initiated, direct pressure is applied by placing the gauze on the area through third penetration 16 to stop the bleeding. The gauze is also useful for manipulating the heart and applying slight pressure to TMR entrance sites to avoid excessive bleeding.

In one embodiment, articulating scope is initially positioned in penetration 14 and REVASCULARIZATION channels are created at the desired location, such as the apex 20. Preferably the energy delivery device is inserted through the working channel of the articulating scope adapted for the procedure. The articulating scope also may be initially positioned in penetration 12 or 16. Once the desired number of REVASCULARIZATION channels is formed, the articulating scope is removed. Graspers and needle holders, or other instruments, are introduced through one of the penetrations to stitch back the pericardial sac, if necessary. A check is made to ensure that there is no bleeding, trocars are removed and the penetrations closed. It will be recognized that the procedure will vary, depending upon the condition of the heart and the site of the procedure.

Figure 3:
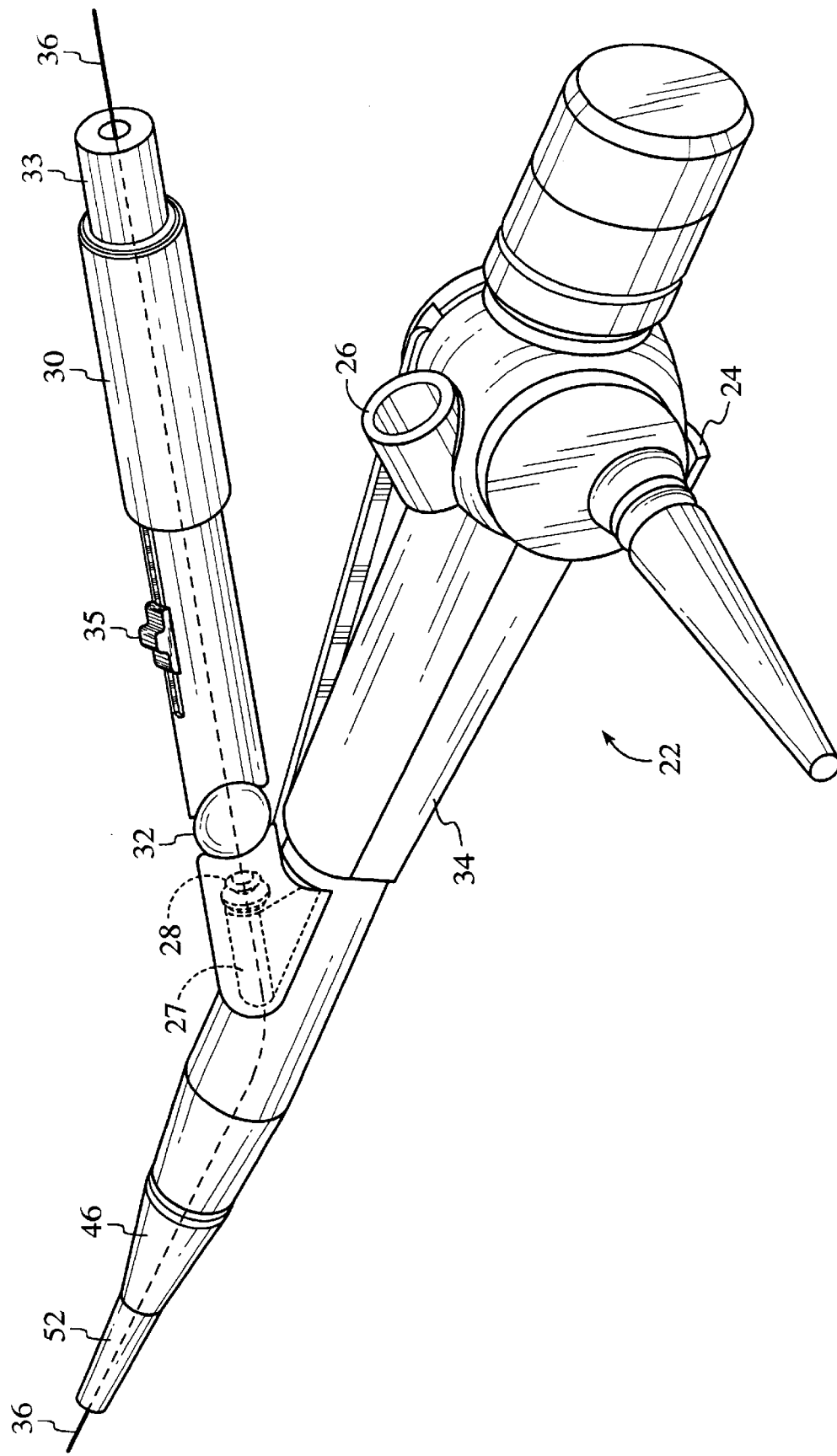
FIG. 3 is a top and side perspective view of the rigid portion of an articulating scope of the present invention.

Referring now to FIG. 3, an articulating scope 22 suitable for use with the present invention is illustrated. In one embodiment, articulating scope 22 includes a flexible distal portion which provides for a coupling of a surface of the heart to the distal portion of articulating scope 22 to provide for the stability of the apparatus on the beating heart. Articulating scope 22 has an articulating distal portion that is coupled to a control member 24 to provide articulation. Articulation can be by a mechanical force, via electronic motion, and the like. Control member 24 can include a straightening device that is coupled to a pre-bent shaft of articulating scope. Movement of control member 24 causes deflection, including articulation, of the generally flexible working end of the scope in a manner well known in the art. Articulating scope 22 may also include a vacuum port 26 configured to be coupled to a vacuum source. The coupler may be a two way valve to provide both vacuum and flushing solutions. Application of a vacuum couples the distal portion of articulating scope 22 to the heart. Other methods of coupling include but are not limited to use of a piercing tip to anchor to the epicardium or by providing a patterned, textured gripping surface at the distal tip. Articulating scope 22 can be supported by a scope holder that is table mounted or mounted to the patient.

An access port 27 is provided for the introduction of tools and instruments including but not limited to scissors, graspers, fiber optic tools, suture mechanisms. An adaptor 28, including but not limited to rigid or articulating couplers/fittings extending at any angle to the longitudinal axis of scope 22, couples access port 27 with a handle 30. Handle 30 is configured to move in an up and down fashion and provides a working channel for the introduction of an energy delivery device. The coupling of adaptor 28 to articulating scope can be achieved in different ways, however, in one embodiment, a ball joint socket 32 is employed to allow movement of the handle 30. A standard scope holder (not shown) and adapter can be used to cradle and stabilize articulating scope 22 and attaches along a surface 34 of articulating scope 22 and to the operative table. Additionally, a similar standard scope holder can also be used to cradle the rigid scope. Coupled to handle 30 is a energy delivery device retention member 33. An energy delivery device advancement member 35 is actuated by the thumb and advances and retracts an energy delivery device 36 through articulating scope 22 to and from a selected site. A proximal portion of retention member 33 is a compression fitting that can lock energy delivery device 36 in position so that its advancement//retraction distances are controlled solely by member 35. Retention member includes a thumb activated knob which may be tightened and loosened.

Control member 24 moves in connection with the motion of handle 30. Control member 24 provides the desired degree of deflection at the distal portion of articulating scope 22. The physician's hand is on handle 30 which thus controls member 24. Sufficient friction is provided to retain energy delivery device 36 at its desired location without the physician having to move his/her finger or thumb to control member 24.

Handle 30 also provides for easy deflection/positioning of the flexible distal tip of scope 22. Once a desired site is selected, the physician's hand remains on handle 30 and with wrist motion moving joint socket 32 can provide multiple movements of the distal tip of the scope 22 bearing the energy delivery device 36. The physician's other hand remains on a rigid or semi-rigid section 38, which in one embodiment is a cable, (see FIG. 8) of the distal portion of articulating scope 22 that is associated with a flexible portion of articulating scope 22 to provide gross placement of the tip of the scope movement. This provides single hand movement of energy delivery device 36. The physician's hand on handle 30 articulates the distal portion of articulating scope 22 and advances the physician's finger on member 35 and retracts energy delivery device 36.

Figure 4:
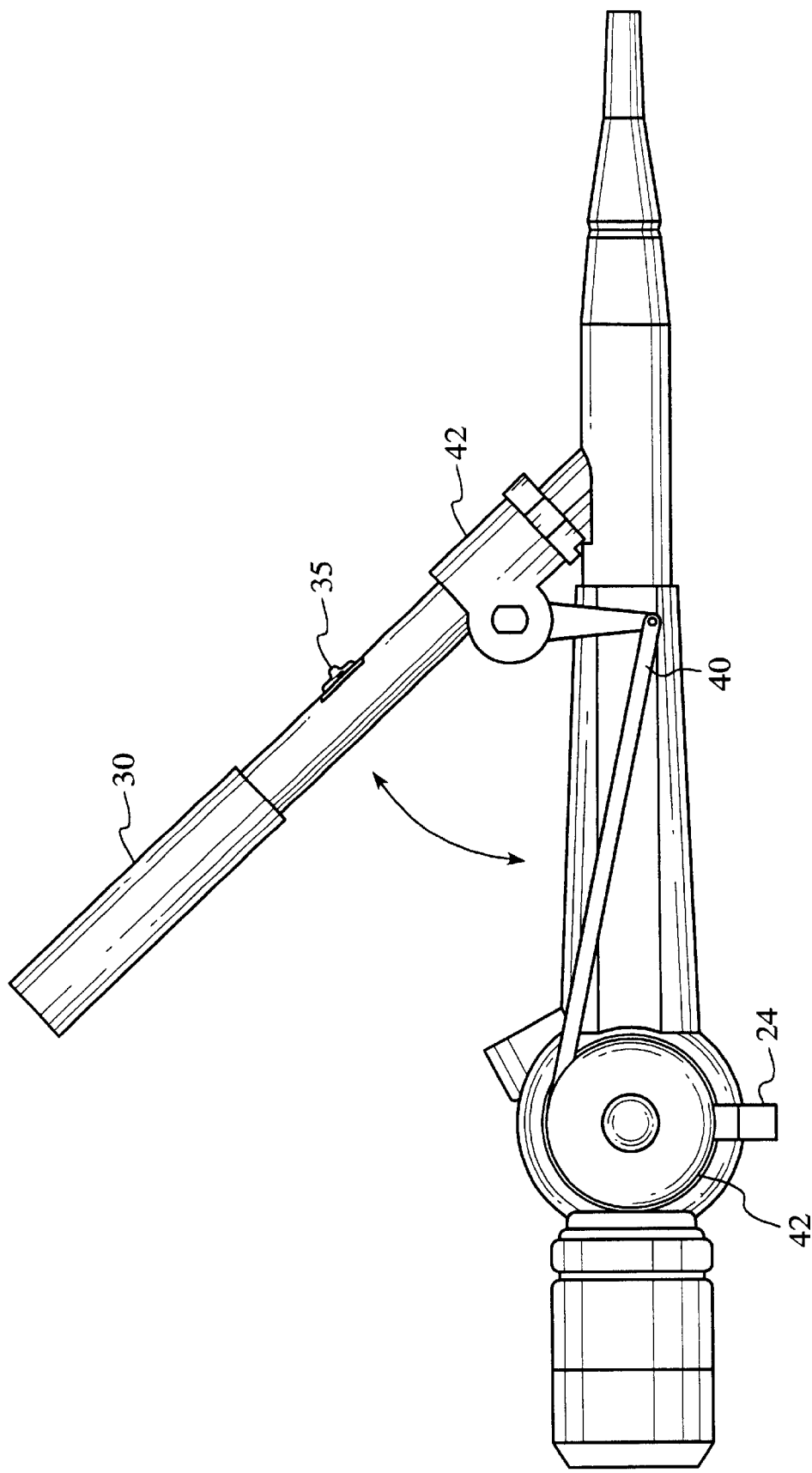
FIG. 4 is a side perspective view of the articulating scope of FIG. 3.

One embodiment of articulating scope 22 is shown in FIG. 4 with a mechanical linkage 40 to provide single handed placement and advancement/retraction of waveguide 36. A ball joint is replaced with a knuckle joint 42 to allow handle 30 to be moved in an up and down motion. Mechanical linkage 40 is coupled to control member 24. A friction imparting device 42, including but not limited to a friction plate, is included as a separate element. Alternatively, the function of providing friction can be included in knuckle joint 42 and included as part of mechanical linkage 40 to control member 24.

Figure 5:
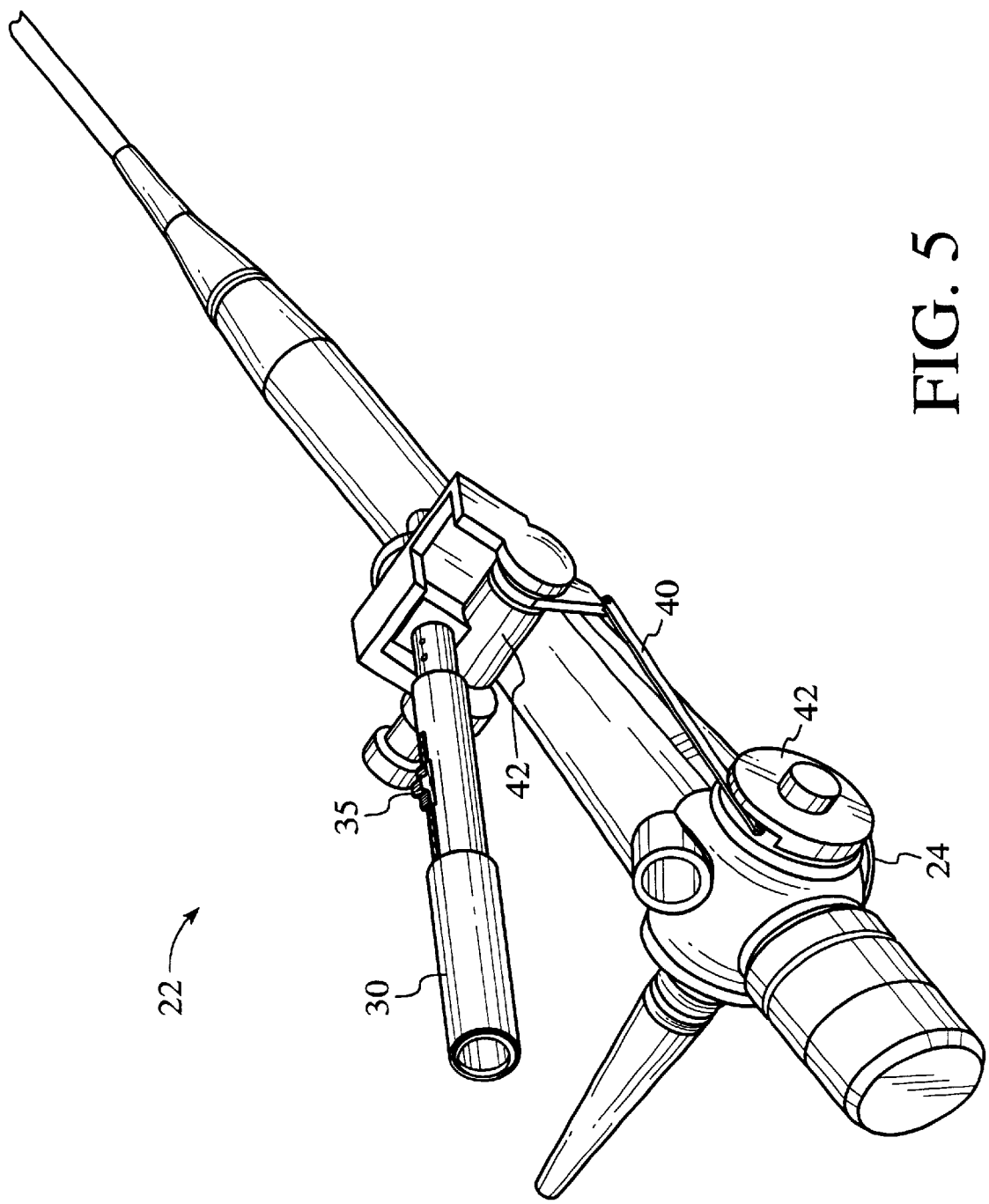
FIG. 5 is a top and first side perspective view of a mechanical linkage of the articulating scope of FIG. 3.
Figure 6:
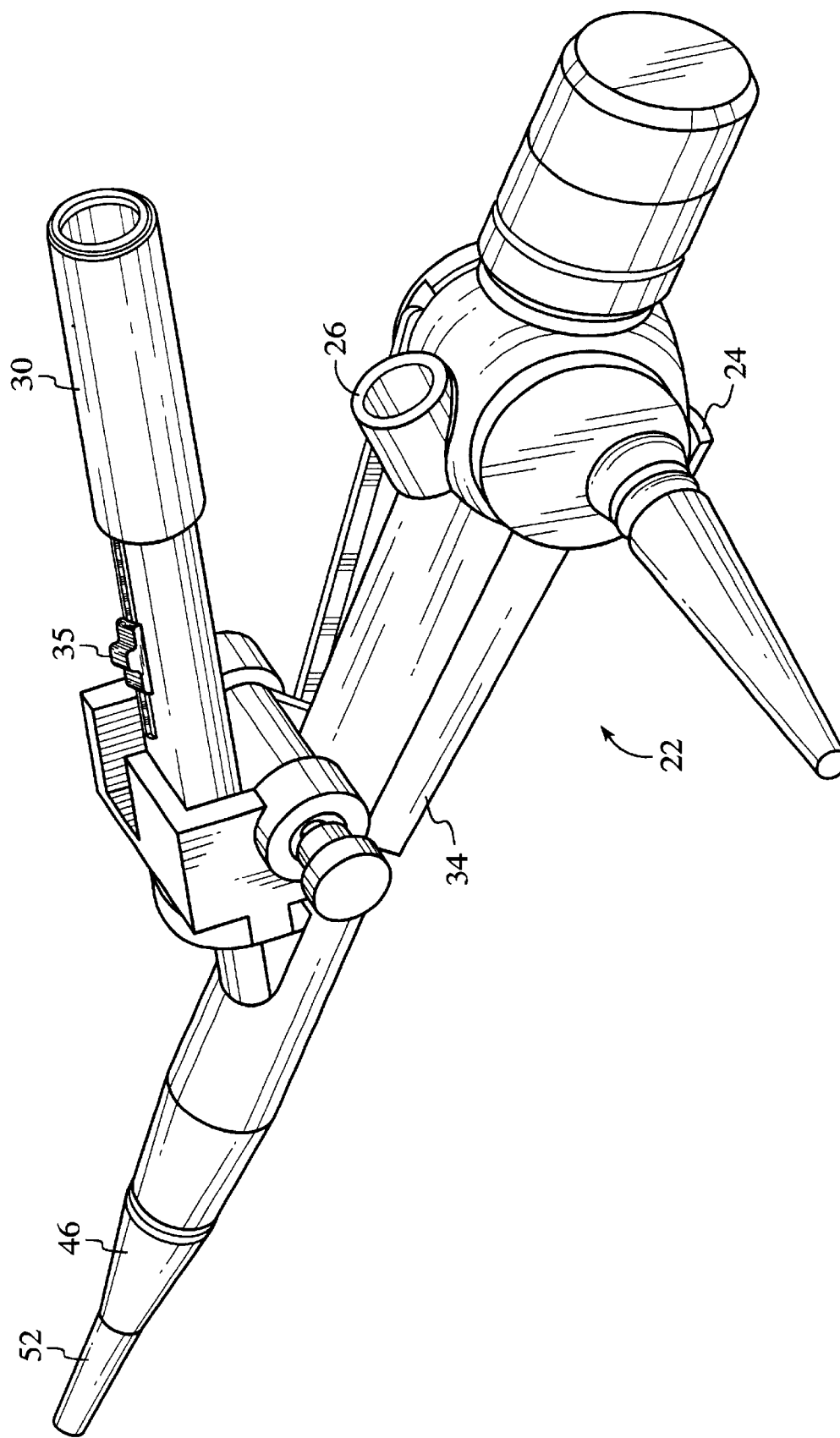
FIG. 6 is a top and second side perspective view of the mechanical linkage of the articulating scope of FIG. 3.
Figure 7:
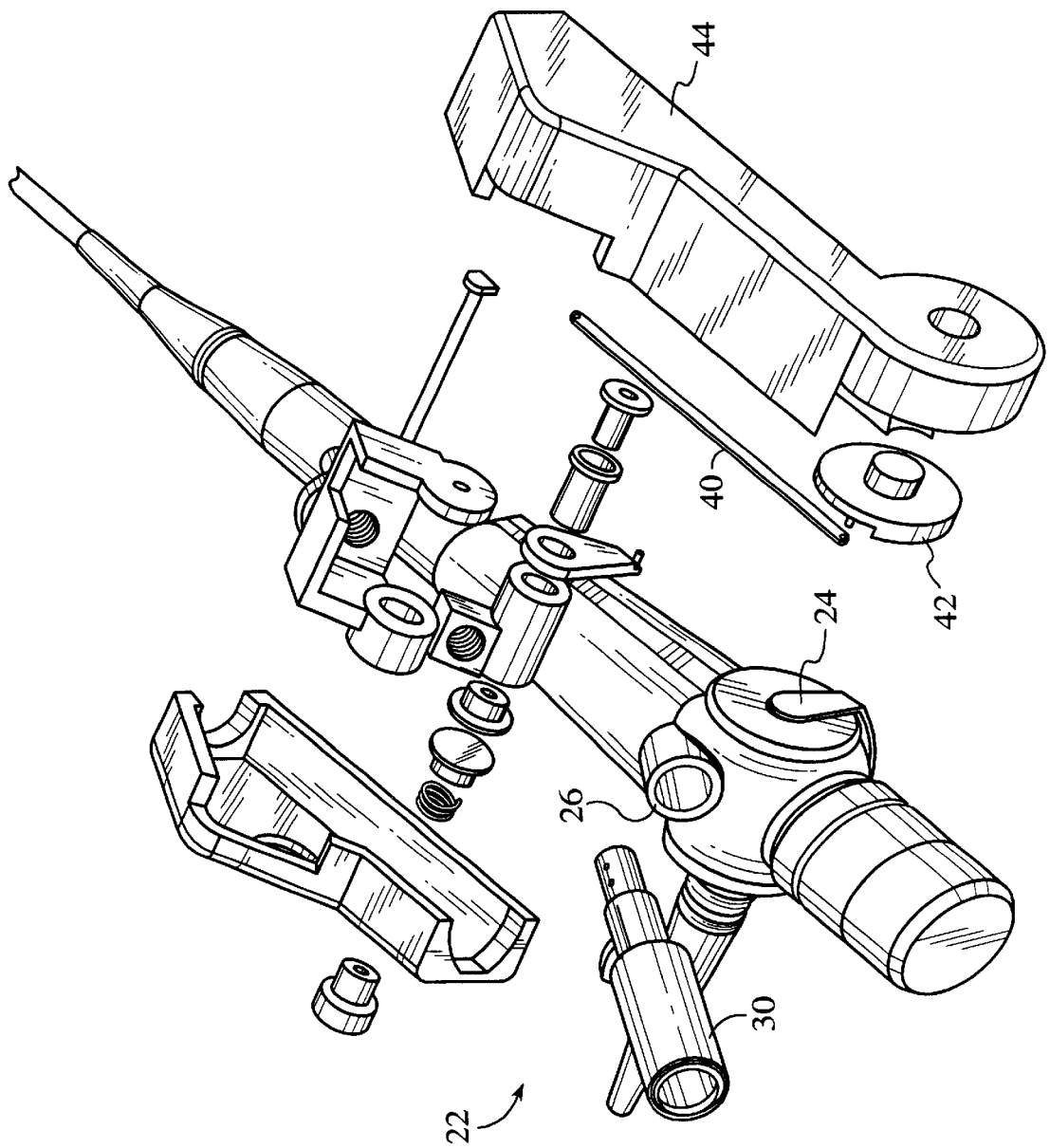
FIG. 7 is an exploded view of the articulating scope of FIG. 3.

FIGS. 5 and 6 illustrate different perspective view of articulating scope 22. FIG. 7 is an exploded view of articulating scope 22 and includes a cover 44 which covers mechanical linkage 40. As can be seen, the linkage allows the physician to move the position of the distal tip of the scope on the heart to create additional channels without removing his hand from the handle which controls energy delivery device 36.

Figure 8:
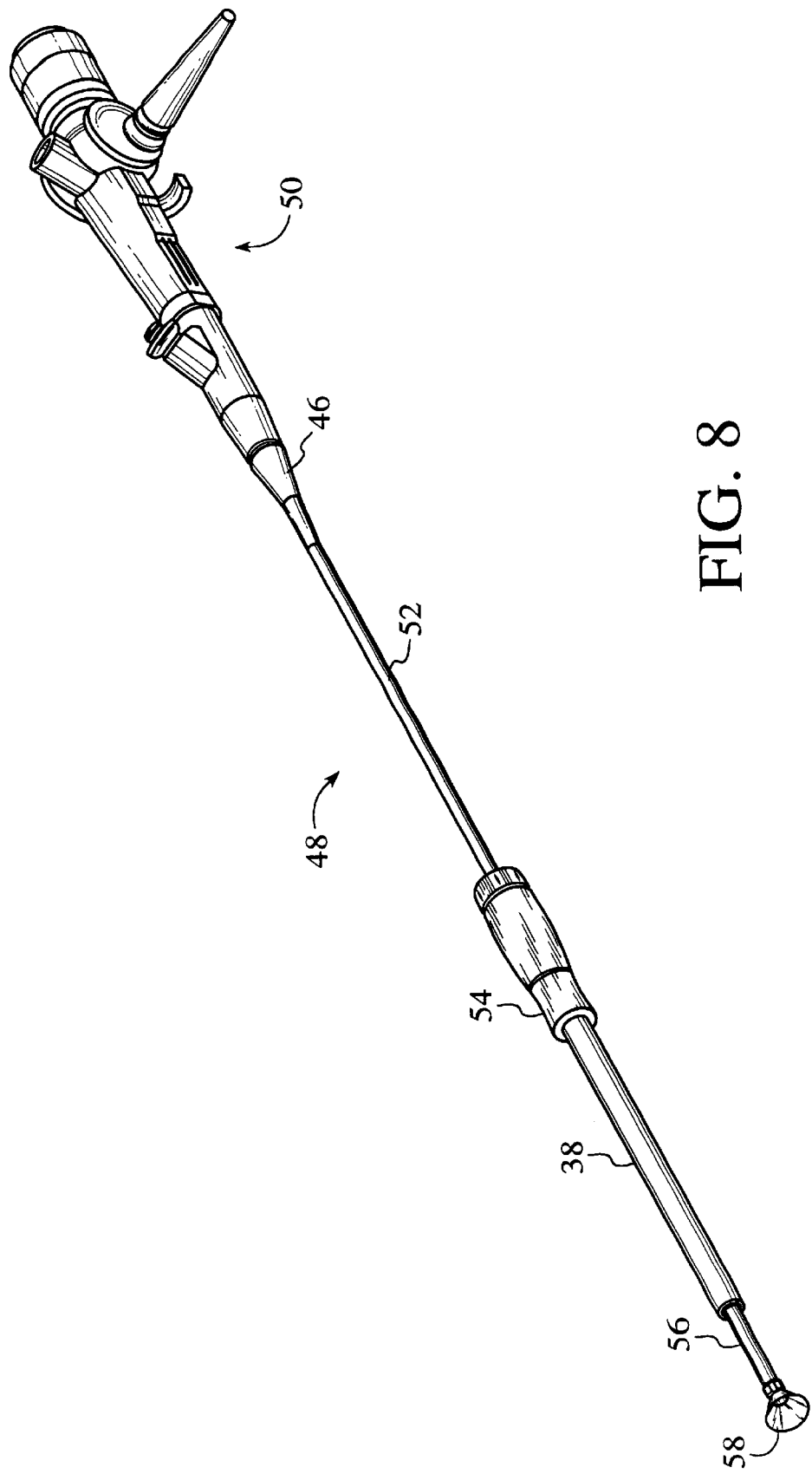
FIG. 8 is a perspective view of the rigid and flexible portions of the articulating scope of FIG. 3.

Referring now to FIG. 8, a strain relief member 46 couples a flexible portion, generally denoted as 48 to a rigid portion 50 of articulating scope 22. A flexible tubular member 52 carries energy delivery device 36 and is coupled to rigid or semi rigid member 38 with a second strain relief member 54. Strain relief member 54 may be a compression fitting. Rigid member 38 provides steerability and stability for accurate placement of energy delivery device 36 as it is advanced. Rigid member 38 also minimizes rotation and axial movement.

Coupled to a distal end of rigid member 38 is a flexible member 56 which maintains flexibility at the distal tip. A silicon rubber, plastic material, elastomer, or other flexible member permits maximum articulation of energy delivery device 36 when control member 24 is activated. Flexible member 56 is generally very thin silicon rubber or flexible plastic in order to continue to provide articulation and good movement of energy delivery device 36. The thinness of flexible member 56 permits full or near full articulation of energy delivery device 36. If flexible member 56 is too thick, then articulation may be sacrificed. Additionally, the distal tip of flexible member 56 is configured to hold off the optics of articulating scope 22 from the surface of the heart in order to help maintain a specified field of view and maintain focus. Flexible member 56 assists in keeping the optics in focus, reduces smudging of the optics, and allows access to substantially all walls of the heart (lateral anterior and posterior). Flexible member 56 is preferably made of a material that permits the passage of ambient light which provides enhanced viewing.

In one embodiment, a cup member 58 is coupled to a distal end of flexible member 56. Cup member 58 is coupled to a vacuum source and becomes attached to a wall of the heart. Cup member 58 provides a broad surface which becomes locked on the wall of the heart. While the heart is beating the ability of locking articulating scope 22 via cup member 56 and the use of a vacuum source provides mechanical stability when energy is delivered from an energy source through energy delivery device 36 to a selected target site. Cup member 58 helps to keep the optics clean and provides a protective shield if the distal end of energy delivery device 36 has a piercing point which can scratch the heart.

In other embodiments, cup member 58 is replaced with a flange with a gripping surface that provides the locking function.

In various embodiments, the trocar introduced in any of penetrations 12, 14 or 16 can be an introducer made of TEFLON, polypropane, and the like. Slits may be formed in the introducer to permit cup member 58 to be easily retracted into an interior lumen of the trocar. It will be understood by those skilled in the art that the procedures described above are examples only. For instance, the control of the articulating scope need not be coupled to control fiber advancement or fiber advancement may be controlled from the scope. Additionally, any number of introducer devices may be inserted as needed.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An articulating scope apparatus for performing transmyocardial revascularization comprising:

a first working channel having an articulating distal portion and a proximal control member;

a handle having a distal portion and a second working channel in communication with the first working channel;

a linkage member coupling the distal portion of the handle to the control member;

whereby both movement of the handle, effecting articulation of the distal portion by the control member, and movement of a working device adapted for introduction within the first and second working channel can be controlled with a single hand.

2. The apparatus of claim 1 further comprising a working device retention member and a working device movement member coupled to a proximal portion of the handle; and a working device locking member coupled to the retention member.

3. The apparatus of claim 2 wherein the linkage member is a ball and socket joint.

4. The apparatus of claim 2 wherein the linkage member is a mechanical linkage.

5. The apparatus of claim 4 wherein the mechanical linkage is a knuckle joint.

6. The apparatus of claim 2 further comprising a working device.

7. The apparatus of claim 6 wherein the working device is an energy delivery device configured to be coupled to an energy delivery source.

8. The apparatus of claim 7 wherein the energy delivery device is a laser wave guide, RF electrode, microwave cutter, ultrasound transmitter, mechanical coring device, or fluid jet.

9. The apparatus of claim 7 wherein the energy delivery device is a laser energy delivery device.

10. The apparatus of claim 7 further comprising an anchor element at the articulating distal portion.

11. The apparatus of claim 10 wherein the anchor element is gripping surface.

12. The apparatus of claim 10 wherein the anchor element is piercing tip.

13. The apparatus of claim 10 further including a vacuum port coupled to vacuum source and wherein the anchor element is a suction cup member.

14. The apparatus of claim 2 wherein the articulating scope is a digital scope having a visualization mechanism at the articulating distal portion.

15. The apparatus of claims 14 wherein the visualization mechanism is a CCD camera based system.

16. The apparatus of claim 2 wherein the control member provides articulation of the distal portion by mechanical force or via electronic motion.

17. The apparatus of claim 16 further including a straightening device coupled to the control member and a shaft of the articulating scope.

* * * * *